United States Patent [19]

Paul

[11] Patent Number: 5,080,662

[45] Date of Patent: Jan. 14, 1992

[54] SPINAL STEREOTAXIC DEVICE AND METHOD

[76] Inventor: Kamaljit S. Paul, 1204 Maria La., Menasha, Wis. 54952

[21] Appl. No.: 441,648

[22] Filed: Nov. 27, 1989

[51] Int. Cl.⁵ ............................................. A61B 19/00
[52] U.S. Cl. ................................................. 606/130
[58] Field of Search ........................................ 606/130

[56] References Cited

U.S. PATENT DOCUMENTS

| | | | |
|---|---|---|---|
| 4,350,159 | 9/1982 | Gouda | 606/130 |
| 4,592,352 | 6/1986 | Patil | 606/130 |
| 4,653,509 | 3/1987 | Oloff et al. | 606/130 X |
| 4,723,544 | 2/1988 | Moore et al. | 606/130 |
| 4,750,487 | 6/1988 | Zanetti | 606/130 |

FOREIGN PATENT DOCUMENTS

| | | | |
|---|---|---|---|
| 2115121 | 10/1972 | Fed. Rep. of Germany | 606/130 |
| 3804491 | 6/1989 | Fed. Rep. of Germany | 606/130 |
| 818711 | 8/1959 | United Kingdom | 606/130 |

Primary Examiner—Michael H. Thaler
Attorney, Agent, or Firm—Fuller, Ryan & Hohenfeldt

[57] ABSTRACT

A stereotaxic device for directing a puncturing tool toward a designated target within a patient. A tool guide is provided for directing the puncturing tool toward the target, and a positioning device for positioning the tool guide anywhere on a hemispherical surface from which to direct the puncturing tool toward the target. The positioning device includes an arcuate slider associated with the tool guide, with the designated target at the center of the arc of the slider. A rotator is slidably connected to the arcuate slider for permitting the arcuate slider to slide while maintaining the tool guide at the hemispherical surface. Adjustments are permitted by the following structure to the position of the rotator along mutually perpendicular X, Y and Z axes with respect to the designated target, that rotator being journaled for rotation about one of the axes. A pair of guide rails are affixed to a rectangular base plate. A pair of support columns are slidably connected at one end to a respective one of the guide rails to permit sliding movement therealong. Y-axis controls change the distance between the opposite end of the support columns and the base plate. Horizontal slider rods connect together the support columns at the opposite ends, and slidably carry the rotator. Targeting devices are provided for positioning the support columns, rotator and transfer slider so that the tool guide always guides the puncturing tool to the designated target.

3 Claims, 3 Drawing Sheets

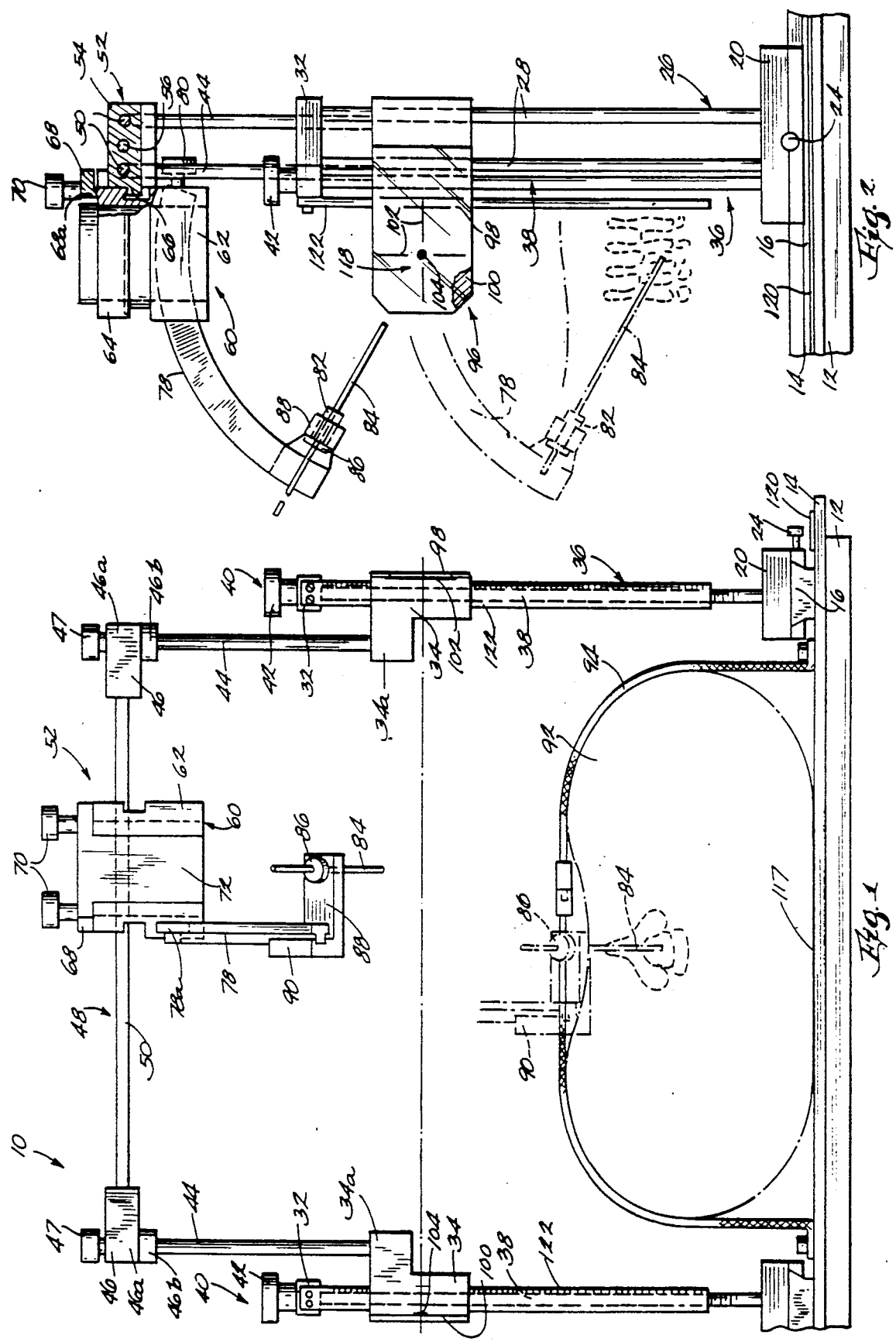

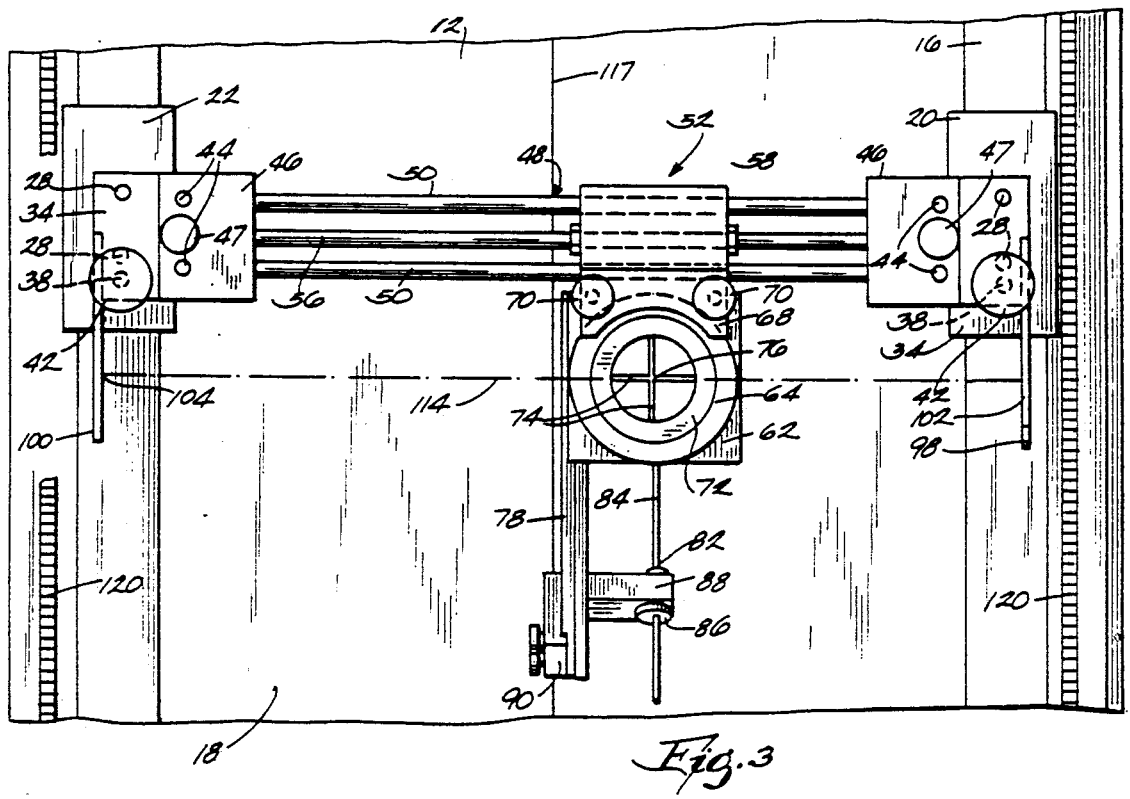
Fig. 3
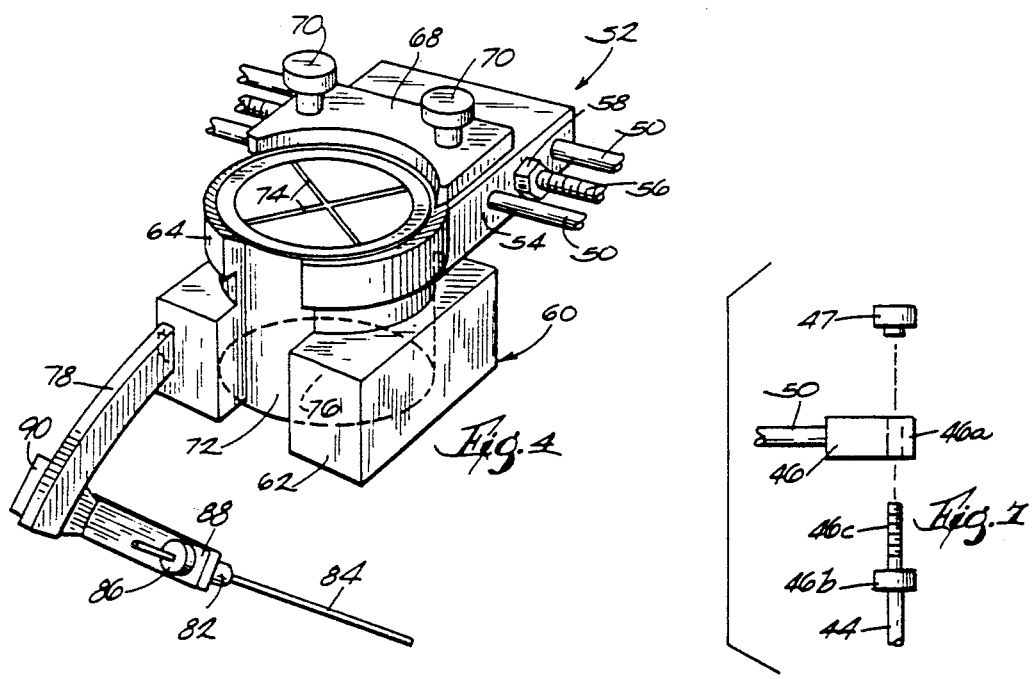
Fig. 4
Fig. 2

SPINAL STEREOTAXIC DEVICE AND METHOD

BACKGROUND OF THE INVENTION

This invention relates to medical instruments, and in particular to devices for directing puncturing devices toward a desired target inside the body of a patient.

A common problem among sufferers of back pain is prolapsed lumbar intervertebral disc, wherein a portion of the disc between two vertebrae in the lower back prolapses outward and causes pressure on a nerve. In the past, the only successful treatment had been major surgery. Because of the substantial trauma caused by such surgery, however, it was not uncommon for the patient to experience a recovery period of ten to twelve weeks before he could return to his previous employment. Recently a new technique has been developed wherein nucleus material of the prolapsed disc is excised by percutaneous aspiration. The disc nucleus is soft and jelly-like in consistency. It can thus be resected and aspirated by use of a specially designed cannula. The aspiration cannula is inserted into the nucleus of the prolapsed disc with the aid of a guide wire or needle prior to connecting it to the aspirating machine. The major problem, however, is that exacting placement of the needle is crucial to avoid nerve damage.

Since the herniation of the disc most frequently occurs between the fourth and fifth lumbar vertebrae, or between the fifth lumbar and sacral vertebrae, the insertion of the needle is very difficult. Particularly in the latter case, the needle must be inserted not only at an angle to the vertical, but also at an angle relative to the sagittal axis, in order to avoid the protective iliac crest of the sacrum. Preferably the needle is inserted at about eight centimeters away from the midline, on the coronal plane of the prolapsed disc level, at an angle of about 45 degrees. In the past, the needle has been inserted by trial and error, while monitoring its placement by fluoroscopic examination.

The difficulty resulting from this requirement of the compound angle is referred to in Moore, et al, U.S. Pat. No. 4,723,544. The structure disclosed in that patent, however, presents other difficulties relating to structural rigidity and integrity. Another structure intended generally for the same purpose is disclosed in Zanetti, U.S. Pat. No. 4,750,487. Both the Moore and the Zanetti structures provide for the attachment of the apparatus to one side of the operating table. A structure is required which provides more structural rigidity and flexibility in placement of the cannula than either of these structures, and still facilitates the attainment of the required compound angle In addition, a structure is required which can provide guidance to the needle from either side of the patient without requiring the removal and replacement of the structure to change sides.

This invention relates to improvements over the apparatus described above and to solutions to some of the problems raised thereby.

SUMMARY OF THE INVENTION

The invention relates to a stereotaxic device for directing a puncturing tool, and particularly a guide needle, toward a designated target within a body cavity of a patient The invention includes a tool guide for directing the puncturing tool toward the designated target, and positioning means for positioning the tool guide anywhere on a hemispherical surface from which to direct the puncturing tool toward the designated target. The positioning means includes arcuate slider means associated with the tool guide, with the designated target at the center of the arc of the arcuate slider means. Rotator means are slidably connected to the arcuate slider means for permitting the arcuate slider means to slide while also permitting a full 360 degrees of rotation, thus maintaining the tool guide at the hemispherical surface. Adjusting means are provided for adjusting the position of the rotator means along mutually perpendicular X, Y and Z axes with respect to the designated target, that rotating means being journaled to the adjusting means for rotation about one of the axes. Those adjusting means generally include a rectangular base plate and a pair of parallel guide rails affixed thereto. A pair of support means are oriented substantially normal to the base plate, each slidably connected at one end to a respective one of the guide rails to permit sliding movement of the support means along the guide rails in a Z direction. The support means includes Y-axis control means for changing the distance between the opposite end of the support means and the base plate. The opposite end is thus movable in a Y direction normal to the Z direction. The invention further provides crossing means for connecting together the pair of support means at the opposite ends thereof. The crossing means are positioned generally over the patient and oriented substantially parallel to the plane of the base plate and normal to the support means. The invention also includes targeting means for positioning the support means, crossing means and transfer slider means so that the tool guide guides the puncturing tool to the designated target. The targeting means includes Y-Z targeting means for positioning the support means and the crossing means with respect to the base plate, and X-axis targeting means for positioning the transfer slider means with respect to the crossing means.

Other objects and advantages of the invention will become apparent hereinafter.

DESCRIPTION OF THE DRAWING

FIG. 1 is a front elevation view of a stereotaxic device constructed according to a preferred embodiment of the invention.

FIG. 2 is a side elevation view of the stereotaxic device shown in FIG. 1, partially in section.

FIG. 3 is a top plan view of the stereotaxic device shown in FIG. 1.

FIG. 4 is an isometric view of the portion of the stereotaxic device shown in FIG. 1 which permits lateral movement and rotation of the needle support.

FIG. 7 is an exploded side view of an end block assembly.

DESCRIPTION OF THE PREFERRED EMBODIMENT

Figure 5:
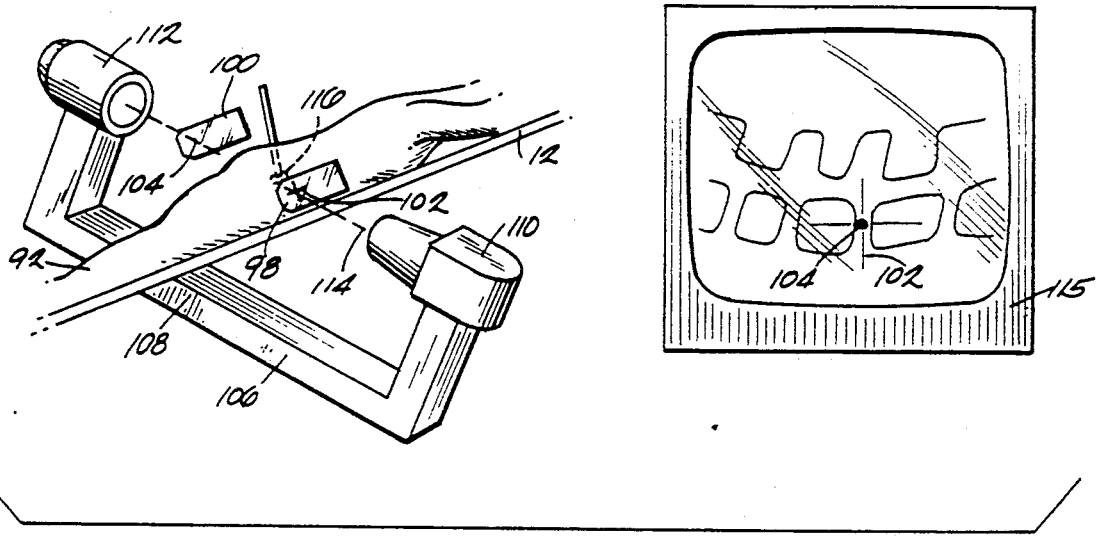
FIG. 5 is an isometric view of the device being aligned in the Y and Z directions according to the invention.

In the following description, there will be referred to three axes or directions, all mutually perpendicular, a Z-axis, a Y-axis and an X-axis, or longitudinal, vertical and lateral directions, respectively. Although the invention is not to be limited by these direction references in the following description, most commonly, for reference purposes, assuming that the patient is lying down when using the following described apparatus, the Z-axis or longitudinal direction will refer to a horizontal direction generally parallel to the medial axis of the patient, the Y-axis or vertical direction will refer to an up-right direction normal to the Z-axis, and the X-axis or lateral direction will refer to a horizontal direction normal to the Z-axis Referring now to FIG. 1, there is shown a stereotaxic device 10 constructed according to a preferred embodiment of the invention. As there shown, the device 10 is entirely portable, and is placed upon an operating table 12 prior to placing the patient on the table for the operation. The device 10 includes a base plate 14 which is generally flat and rectangular in shape. A pair of guide rails 16 and 18 are each secured by suitable means to the base plate 14, spaced apart and generally longitudinally, parallel to each other and to the side edges of the base plate, one along each respective side edge. The guide rails 16 and 18 need not be identical to each other. As shown in FIG. 1, however, both guide rails 16 and 18 are dovetailed. That is, each guide rail 16 and 18 has a relatively narrow base portion which then expands outward to a wider portion at the top.

A pair of base slider-blocks 20 and 22 are slidably mounted, one on each of the guide rails 16 and 18 respectively, for sliding movement along the guide rails, that is, along the Z-axis, with each of the base slider blocks conforming to its respective guide rail. That is, each base slider block 20 and 22 has an internal shape that conforms to the dovetail shape of the respective guide rail 16 and 18. In each case, the mounting is preferably journaled to permit smooth and hitch-free sliding. Each of the base slider blocks 20 and 22 also includes means, such as a set screw 24 which, when tightened, inhibits the sliding motion of the block along the guide rail 16 or 18, in any position determined by the physician as described in more detail below. To this end each set screw 24 is threaded into its respective base slider block 20 or 22, and bottoms on the respective guide rail 16 or 18 when in use, thus preventing relative motion between the respective base slider block 20 or 22 and guide rail 16 or 18. Both slider blocks 20 and 22 are slidable entirely off at least one end of each of the respective guide rails 16 and 18, to permit removal of the rest of the device 10 from the base plate 14, thereby facilitating the movement of the patient onto the base plate for the operation.

Referring now mainly to FIG. 2, projecting vertically upward from each base slider block 20 and 22 are vertical support means 26, which essentially includes two parallel vertical slider rods 28, each anchored in the respective base slider block 20 or 22. Each pair of slider rods 28 in each slider block 20 or 22 is topped in common by a single stop block 32. Each support means 26 further includes a separate vertical slider block 34 slidably mounted on each respective pair of vertical slider rods 28. The invention includes means 36 for controlling the vertical movement of the slider block 34 along the rods 28. In the preferred embodiment, means 36 includes a threaded rod 38, oriented parallel to the rods 28. The bottom end of threaded rod 38 is rotatably anchored in the base slider block 20 or 22 while a portion near the top end is rotatably anchored in stop block 32. The threaded rod 38 is threaded through the slider block 34, so that turning the rod causes the slider block to slide vertically along the slider rods 28. Means 40 are then provided for turning the threaded rod 38, in turn causing the slider block 34 to slide vertically. In one embodiment turning means 40 are knurled knobs 42, one affixed to the top of each of the threaded rods 38. Thus is provided means for changing the vertical height of the vertical support means 26. In the preferred embodiment the vertical support means 26 further include pairs of upper rods 44 affixed to and projecting upwardly from the upper surface of a transverse projection 34a formed in each slider block 34 for that purpose. Each pair of upper rods 44 is topped by a respective end block 46, which is securely affixed to the upper rods. Thus the distance between the respective end block 46 and vertical slider block 34 is fixed and immovable, for reasons to be set forth subsequently.

The two end blocks 46 are connected together by crossing means 48. In one embodiment the crossing means 48 includes a pair of spaced apart, parallel horizontal slider rods 50, shown best in a top view in FIG. 3. Since the rods 50 are connected between the end blocks 46, the rods are generally parallel to the plane of the base plate 14.

The two end blocks 46 are each two-piece end blocks, each having upper portions 46a and lower portions 46b. Each lower portion 46b is securely affixed to the respective upper vertical rods 44, while each upper portion 46a is securely affixed to the horizontal slider rods 50. Each upper portion 46a is connected to the respective lower portion 46b by suitable removable means, such as a nut 47, sized large enough to be removable by hand, threaded onto a bolt 46c projecting upwardly from the top surface of lower portion 46b through the upper portion 46a. Thus is provided another means for partial disassembly of the device 10 to facilitate the movement of the patient onto the operating table 12 for the operation. That is, it is important that the patient, presenting himself for the operation because of back pain which likely already restricts his freedom of movement, not be required to crawl into the device, since to so require would almost certainly be extremely uncomfortable and would thus restrict use of the device to those patients already sufficiently flexible to crawl into it. Rather, by the means disclosed, whether the removal of the upper block portion 46a from the lower block portion 46b, or the sliding of the base slider blocks 20 and 22 off the ends of the guide rails 16 and 18, the device 10 may be quickly partially disassembled to facilitate the movement of the patient onto the operating table 12 for the operation, and then easily and accurately reassembled to begin the operation.

Transverse slider means 52 are slidably mounted on the horizontal slider rods 50, for lateral slidable movement along the rods. In the preferred embodiment the transverse slider means 52 includes a lateral slider block 54 slidably mounted to the horizontal slider rods 50. A third, threaded, lateral rod 56 is also affixed between the end blocks 46, parallel to the other two upper rods 44. In the embodiment shown in FIGS. 2, 3 and 4, the threaded lateral rod 56 is positioned between the two upper rods 44. Threaded lateral rod 56 passes through a smooth bore formed in the lateral slider block 54, and is not threaded therein. As shown best in FIGS. 3 and 4, two nuts 58 are threaded onto the threaded lateral rod 56, one on each side of the lateral slider block 54. Thus is provided means for affixing the lateral slider block in a particular lateral position along the horizontal slider rods 50. This affixing means permits the operator to turn or rotate the nuts away from the lateral slider block 54 to permit free movement of the block and then, when the operator deems the block in the desired position as will be explained more fully subsequently, the nuts are tightened against the block to prevent further movement.

Rotator means 60 are connected to the lateral slider block 54 so as to be rotatable about a vertical axis after being moved to the desired position as referred to above. In the preferred embodiment, the rotator means 60 includes an arc holder 62, the upper part of which is generally cylindrical in shape. The arc holder 62 includes an annular projection 64 about the entire periphery of the top end of the arc holder, the cross sectional shape of the projection being dove-tailed. As shown best in FIG. 2, the lower surface of the projection 64 fits onto a shelf 66 provided for that purpose in the front face of lateral slider block 54.

A clamp plate 68, FIGS. 2, 3 and 4, is provided to secure the annular projection 64 and hence the arc holder 62 in place. The clamp plate 68 is secured to the top surface of the lateral slider block 54 by any suitable means which is capable of being fastened and loosened without complete removal. In the preferred embodiment, the clamp plate 68 is secured by a pair of finger screws 70 inserted through respective openings provided for that purpose in the clamp plate and threaded into the top surface of the lateral slider block 54. As shown in FIG. 2, the clamp plate 68 projects beyond the edge of the lateral slider block 54 on the side toward the arc holder 62, and includes an arcuate groove 68a in its lower surface for fitting closely with the upper surface of the annular projection 64 of the arc holder 62. Hence with the finger screws 70 slightly loose, the arc holder 62 may without limit be rotated smoothly and slidingly with respect to the lateral slider block 54. Once the arc holder 62 is rotated to the desired position, the finger screws 70 are tightened down and the arc holder is no longer rotatable.

Rotator means 60 further includes a cylindrical insert 72 inserted inside the annular projection 64. The cylindrical insert 72 has flat top and bottom surfaces which are clear, and which are provided with X-axis sighting means 73, such as cross-hairs 74 at the top surface and a dot 76 in the bottom surface, to aid in positioning the transverse slider means 52.

One side of the arc holder 62 includes an arcuate groove 62a, into which is slidably mounted a smooth arc member 78. As shown in FIG. 1, the arc member 78 preferably has a T-shaped cross-section, the cross bar 78a of the T being positioned toward the arc holder 62, and fitting into the groove 62a, which has a similar T-shape to accommodate the arc member. Also, the radius of the arc member 78 corresponds to the radius of the groove 62a. A set screw 80 (FIG. 2) may be provided as means for locking the arc member 78 in place with respect to the arc holder 62.

The invention also calls for a tool guide 82 for guiding a piercing tool 84 such as a cannula when using the device 10. In the preferred embodiment, the tool guide 82 is a tube having an inside diameter of a size to closely accommodate the outside diameter of the piercing tool 84. The outside of the tool guide 82 includes a collar 86 which acts as a stop when the tool guide is inserted into a support arm 88. The support arm 88 is in turn slidably mounted to the arc member 78 by means of tool guide slider 90. The tool guide slider 90 is mounted to the side of the arc member 78 opposite to the side by which the arc member is mounted to the arc holder 62. Thus the tool guide slider 90 may slide in an arcuate path along the entire length of the arc member 78, and at the same time the arc member 78 may slide its entire length with respect to the arc holder 62.

The device 10 is designed to be used and operated only by physicians fully familiar with the physiology and pathology of the spine. Such physicians should also be properly qualified to perform spinal surgical procedures.

In operation, a patient 92 requiring a discectomy is placed upon the base plate 14 and secured there by any suitable means constructed of X-ray translucent material, such as fabric straps 94, secured together by suitable removable means such as hook-and-pile fasteners. As can be seen by comparing FIG. 5 and FIG. 2, the device 10 is first aligned in the Y and Z directions by use of Y-Z sighting means 96 attached to the vertical slider blocks 34. The Y-Z sighting means 96 include flat plates 98 and 100 each attached to a respective one of the vertical slider blocks 34. Each of the flat plates 98 and 100 is constructed of X-ray translucent material. It may also be helpful if the flat plates 98 and 100 are constructed of a rugged but transparent material, such as Lexan or plexiglass, to enhance visual alignment. In the most preferred embodiment one of the flat plates 98 includes cross hairs 102 of X-ray opaque material, while the other of the plates 100 includes a small ball or dot 104, also of an X-ray opaque material.

Figure 6:
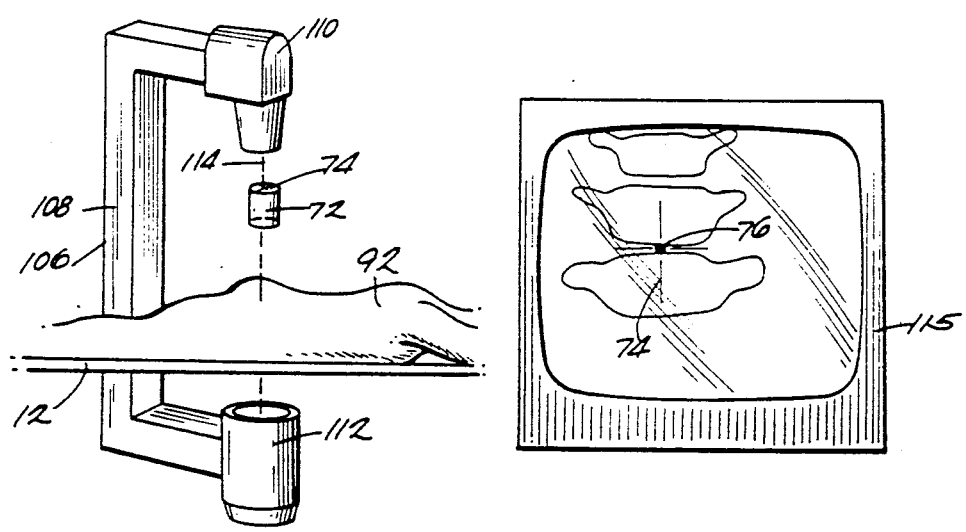
FIG. 6 is an isometric view of the device being aligned in the X direction according to the invention.

A generally conventional C-arm image intensifier 106 is shown in FIGS. 5 and 6, having a C-arm 108, an X-ray projector 110 at one end of the C-arm and a fluoroscope 112 at the other end aligned with the X-ray projector, creating a line-of-sight 114 between the two. A fluoroscopic display 115 is connected to the fluoroscope 112 to show the view produced by the intensifier 106. According to the invention, as indicated above, the patient 92 is placed on the base plate 14 on the operating table 12. Before securing the patient 92 by means of straps (FIG. 1) as described earlier, the intensifier 106 is activated and the patient is aligned with the device 10. This alignment is done by aligning the spinous process of the patient with a wire 117 (FIGS. 1 and 3), or other long, thin member made of X-ray opaque material, embedded in the base plate 14, parallel to and generally centered between the guide rails 16 and 18.

The C-arm 108 is then maneuvered into the position shown in FIG. 5 so that the line-of-sight 114 passes laterally through a target 116 within the patient, in this case the spinal disc on which the discectomy is to be performed, to give a lateral view as shown on the display 115. The device 10 is then maneuvered, along the Z-axis by moving the slider blocks 20 and 22 along the guide rails 16 and 18, and along the Y-axis by moving the vertical slider blocks 34 along the vertical slider rods 28, until it can be seen on the display 115 that the Y-Z sighting means 96 is aligned with the line-of-sight 114. In the preferred embodiment, the device 10 includes Z-axis rulers 120 (FIGS. 1 and 3) attached to the base plate 14 adjacent to and parallel to each of the guide rails 16 and 18. These rulers 120 are provided to permit the operator to ensure that the two base slider blocks 20 and 22 are aligned with each other, that is, at the same position along the respective guide rails 16 and 18 with respect to each other in the Z direction. Similarly, a Y-axis ruler 122 (FIGS. 1 and 2) is attached to each of the stop blocks 32, reaching downward therefrom, so as to permit the operator to ensure that each of the two vertical slider blocks 34 is at the same position along the respective vertical slider rods 28, in order to make sure that the vertical slider blocks 34 are properly aligned with each other in the Y direction. Once the device 10 is properly arranged with respect to the patient 92 by use of sighting means 96 and the base slider blocks 20 and 22 with respect to each other by use of rulers 120, then the set screws 24 are tightened so as to prevent any further movement in the Z direction. The vertical slider blocks 34 are then properly arranged with respect to each other by use of rulers 122, again while maintaining the sighting means 92 on the target 116.

As can be seen by comparing FIGS. 2 and 6, the device 10 is next aligned in the X direction by use of X-axis sighting means 73. The C-arm is maneuvered into the position shown in FIG. 6 so that the line-of-sight 114 passes vertically through the target 116, to give an a-p view on the display 115. The transverse slider means 52 is then moved along the horizontal slider rods 50 until it can be seen on the display 115 that the cross hairs 74 and dot 76 are aligned with the line-of-sight 114. The transverse slider means 52 is then secured in that position by use of nuts 58, as described above.

With the device 10 positioned as just described, the target 116 is aligned with both sighting means 73 and 96. That is, the lines created by sighting means 73 and 96 define a point 118 (shown in a different position in FIG. 2), which in the position just described coincides with the target 116 inside the patient 92. As can be seen in FIG. 2, this point 118 is the center of the arc of the arc member 78. The device 10 is constructed, including the curvature of the arc member 78 as can be seen in FIG. 2, and the length of the support arm 88 as can be seen in FIGS. 1 and 3, so that this point 118 is always pointed to by the tool guide 82, regardless of the position of the tool guide on the arc member 78, regardless of the position of the arc member in the arc holder 62, and regardless of the rotation of the arc holder 62 with respect to the lateral slider block 54. Therefore, once the device 10 is aligned and tightened as described above, with the point 118 being coincident with the target 116, the operator may move the tool guide 82 to practically any usable position, by sliding the tool guide slider 90 along the arc member 78, by sliding the arc member 78 with respect to the arc holder 62, and by rotating the arc holder 62 with respect to the lateral slider block 54, with complete confidence that the target is still coincident with the point, and with complete stability. This functionality is not available in the prior art. Using the structure of the device 10 the operator can, for instance, begin the operation intending to insert the cannula 84 from the left side and, without repositioning the transverse slider means 52 in any way with respect to the patient 92, rotate the arc holder 62 and insert the cannula from the right side. This is but one example of the many benefits provided by this device 10 over the prior art.

While the apparatus hereinbefore described is effectively adapted to fulfill the aforesaid objects, it is to be understood that the invention is not intended to be limited to the specific preferred embodiment of spinal stereotaxic device set forth above. Rather, it is to be taken as including all reasonable equivalents within the scope of the following claims.

I claim:

1. A stereotaxic device for directing a puncturing tool toward a designated target within a body cavity of a patient, comprising:

a tool guide for directing said puncturing tool toward said designated target; and
   positioning means for positioning said tool guide anywhere on a hemispherical surface from which to direct said puncturing tool toward said designated target;
   said positioning means including:
   arcuate slider means having said tool guide slidably mounted to it, with said designated target at the center of the arc of said arcuate slider means;
   rotator means slidably connected to said arcuate slider means for permitting said arcuate slider means to slide while maintaining said tool guide at said hemispherical surface;
   adjusting means for adjusting the position of said rotator means along any one or all of mutually perpendicular X, Y and Z axes with respect to said designated target, said rotator means being journaled to said adjusting means for rotation about one of said axes;
   targeting means for positioning said adjusting means along said Y and Z axes; and
   separate target means for positioning said adjusting means along said X axis, so that said tool guide guides said puncturing tool to said designated target, said X axis targeting means integrated with said rotator means so as to permit a sight to be taken through said rotator means.

2. A stereotaxic device as recited in claim 1 further comprising tightening means for preventing movement of the following: said tool guide with respect to said arcuate slider means, said arcuate slider means with respect to said rotator means, and said adjusting means along said axes, for fixing said puncturing tool in a desired position with respect to said body cavity.

3. A method for directing a puncturing tool toward a designated target within a body cavity of a patient, comprising:

providing a stereotaxic device, comprising:
   a tool guide for directing said puncturing tool toward said designated target; and
   positioning means for positioning said tool guide anywhere on a hemispherical surface from which to direct said puncturing tool toward said designated target;
   said positioning means including:
   arcuate slider means associated with said tool guide, with said designated target at the center of the arc of said arcuate slider means;
   rotator means slidably connected to said arcuate slider means for permitting said arcuate slider means to slide while maintaining said tool guide at said hemispherical surface;
   adjusting means for adjusting the position of said rotator means along mutually perpendicular X, Y and Z axes with respect to said designated target, said rotating means being journaled to said adjusting means for rotation about one of said axes;
   Y-Z targeting means for positioning said adjusting means along said Y and Z axes; and
   Y-axis targeting means for positioning said adjusting means along said Y axis, so that said tool guide guides said puncturing tool to said designated target, said X axis targeting means integrated with said rotator means so as to permit a sight to be taken through said rotator means;

maneuvering a C-arm image intensifier so as to give a lateral view;

adjusting said adjusting means so that said Y-Z targeting means aligns with said target, so as to align said stereotaxic device along said Y and Z axes;

preventing further movement of said adjusting means along said Y and Z axes;

maneuvering said C-arm image intensifier so as to give an a-p view;

sighting said X-axis targeting means through rotator means and adjusting means so that said X-axis targeting means aligns with said target, so as to align said stereotaxic device along said X axis;

preventing further movement of said adjusting means along said X axis; and moving said tool guide by rotating said rotator means and sliding said arcuate slider means with respect to said rotator means so as to obtain a desired angle of entry for said tool.

* * * * *